US012721580B2

(12) United States Patent
Litzenberger

(10) Patent No.: US 12,721,580 B2
(45) Date of Patent: Sep. 1, 2026

(54) FLUOROSCOPY BARRIER

(71) Applicant: CARESTREAM HEALTH, INC., Rochester, NY (US)

(72) Inventor: Michael A. Litzenberger, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 181 days.

(21) Appl. No.: 18/482,236

(22) Filed: Oct. 6, 2023

(65) Prior Publication Data

US 2024/0138784 A1 May 2, 2024

Related U.S. Application Data

(60) Provisional application No. 63/419,734, filed on Oct. 27, 2022.

(51) Int. Cl.
*A61B 6/12* (2006.01)
*A61B 6/42* (2024.01)

(52) U.S. Cl.
CPC .............. *A61B 6/12* (2013.01); *A61B 6/4208* (2013.01)

(58) Field of Classification Search
None
See application file for complete search history.

(56) References Cited

U.S. PATENT DOCUMENTS

| | | | | |
|---|---|---|---|---|
| 5,917,882 | A * | 6/1999 | Khutoryansky | H05G 1/58 378/98.2 |
| 7,866,163 | B2 * | 1/2011 | Ertel | G01T 1/2928 62/3.2 |
| 9,820,703 | B2 * | 11/2017 | Wojcik | A61B 6/4233 |
| 2015/0085990 | A1 * | 3/2015 | Virshup | A61B 6/4283 378/154 |
| 2017/0325761 | A1 * | 11/2017 | Wojcik | A61B 90/39 |
| 2019/0216415 | A1 * | 7/2019 | Wojcik | A61B 6/4283 |
| 2020/0121270 | A1 * | 4/2020 | Wojcik | A61B 6/0407 |

* cited by examiner

*Primary Examiner* — Marcus H Taningco
(74) *Attorney, Agent, or Firm* — Eugene I Shkurko

(57) ABSTRACT

A digital radiographic detector assembly having a housing with a radiopaque sheet and an electrical connector. A digital communication cable is attached to the electrical connector and is configured to be electrically connected to an image receptor positioned in the housing and to a radiographic imaging device. The radiographic imaging device detects that the digital radiographic detector is positioned in the housing and, in response, enables the start of a fluoroscopy exam.

9 Claims, 6 Drawing Sheets

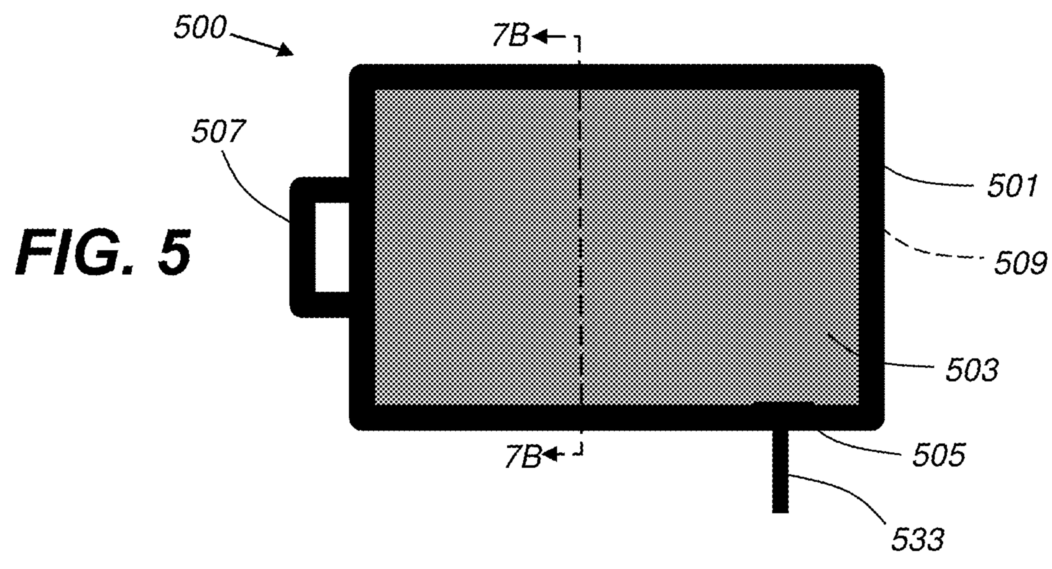
FIG. 5
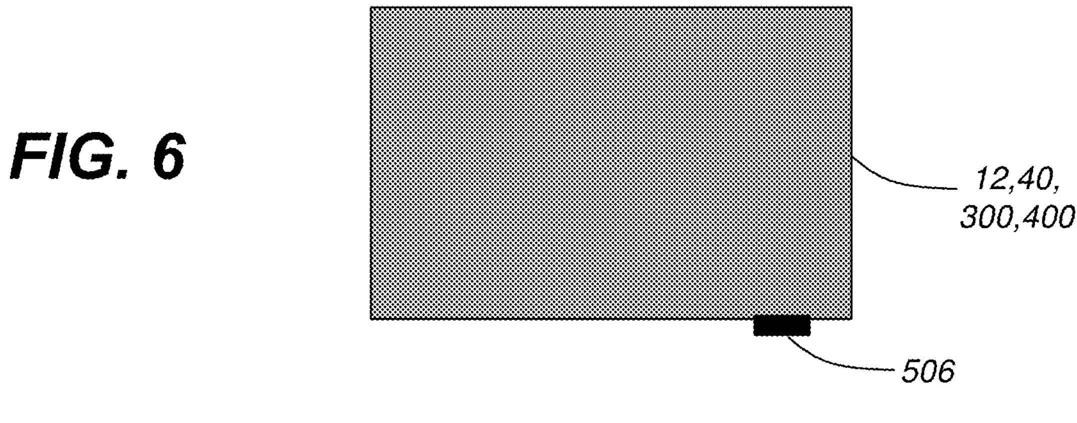
FIG. 6
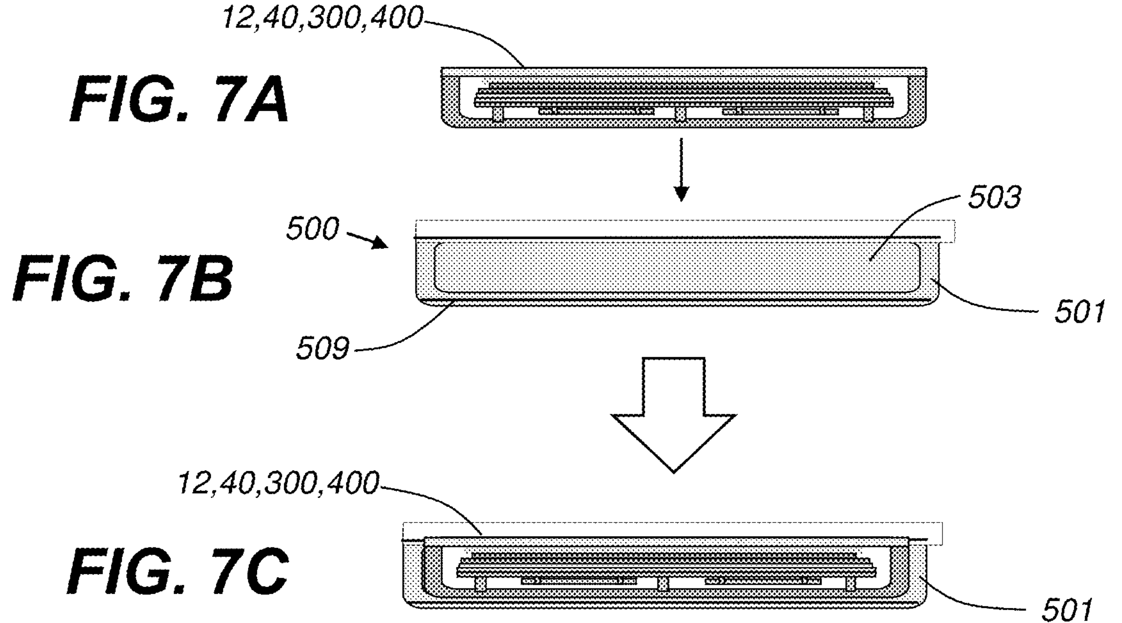
FIG. 7A
FIG. 7B
FIG. 7C

FLUOROSCOPY BARRIER

CROSS REFERENCE TO RELATED APPLICATIONS

This application claims priority to U.S. Patent Application Ser. No. 63/419,734, filed Oct. 27, 2022, in the name of Michael A. LITZENBERGER, and entitled FLUOROSCOPY PRIMARY PROTECTIVE BARRIER WITH TETHER, which is hereby incorporated by reference herein in its entirety.

BACKGROUND OF THE INVENTION

The subject matter disclosed herein relates to ionizing radiation protection during digital radiographic imaging. In particular, to a digital detector and a radiation barrier combination used for fluoroscopy.

A requirement exists for fluoroscopy exams requiring that radiation emitted by an x-ray source, which passes through the patient and the image receptor, be absorbed. This means that a radiopaque radiation barrier must be present during the fluoroscopy exam. Such a barrier must be placed behind the image receptor to absorb and/or block any radiation which passes through the receptor. The imaging device or imaging system must be able to detect the barrier prior to the exam to ensure that it is present.

The discussion above is merely provided for general background information and is not intended to be used as an aid in determining the scope of the claimed subject matter.

BRIEF DESCRIPTION OF THE INVENTION

A digital radiographic detector assembly having a housing with a radiopaque sheet and an electrical connector. A digital communication cable is attached to the electrical connector and is configured to be electrically connected to an image receptor positioned in the housing and to a radiographic imaging device. The radiographic imaging device detects that the digital radiographic detector is positioned in the housing and, in response, enables the start of a fluoroscopy exam.

In one embodiment, a digital radiographic detector assembly includes a housing having a radiopaque material and an electrical connector with an electrical communication cable attached thereto. The housing is configured to receive and hold an image receptor adjacent the radiopaque material. The image receptor is configured to be electrically connected to the electrical connector when positioned in the housing, the radiopaque material extends over an area greater than an area of the image receptor, and the positioned image receptor is detectable using the communication cable.

In one embodiment, a method of operating a digital radiographic detector using a radiographic imaging device includes positioning the digital radiographic detector into a housing, wherein the housing includes a radiopaque layer having an area greater than an area of the digital radiographic detector. The radiographic imaging device confirms the step of positioning the digital radiographic detector into the housing and, in response, enables fluoroscopy imaging using the digital radiographic detector.

In one embodiment, a radiographic imaging device includes an x-ray source and an x-ray image receptor configured to receive x-rays emitted by the x-ray source. The image receptor is positioned in and is electrically connected to a radiopaque housing. The radiographic imaging device controllably and sequentially fires the x-ray source toward the image receptor only when the radiographic imaging device detects that the image receptor is electrically connected to the radiopaque housing.

A radiation barrier is fabricated with substantial radiopaque material to block x-ray radiation. The radiation barrier assembly is combined with a removable image receptor, such as a digital radiographic detector. The barrier assembly may include a permanently affixed electrical communication cable, i.e., a tether, that will electrically connect to the image receptor, or digital detector, on one end and to the imaging device, imaging system console, x-ray processing system, or other suitable imaging control system, on the other end.

The imaging device will detect the presence of the barrier assembly using the communication cable and, in response, enable the radiographic exam to proceed. If the cable is not present, i.e., not detected by the imaging device, or the image receptor is not detected to be electrically connected to the cable, the exam will not be enabled by the imaging device. Since the image receptor must be located in the barrier assembly to be electrically connected to the cable, the exam will only be enabled by the imaging device when the image receptor is placed in the barrier assembly which has the radiation barrier material integrated therewithin.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is a view of an exemplary barrier assembly;

FIG. 6 is a view of an exemplary image receptor or DR detector;

FIGS. 7A-7C illustrate positioning of an image receptor or DR detector in a barrier assembly;

DETAILED DESCRIPTION OF THE INVENTION

Figure 1:
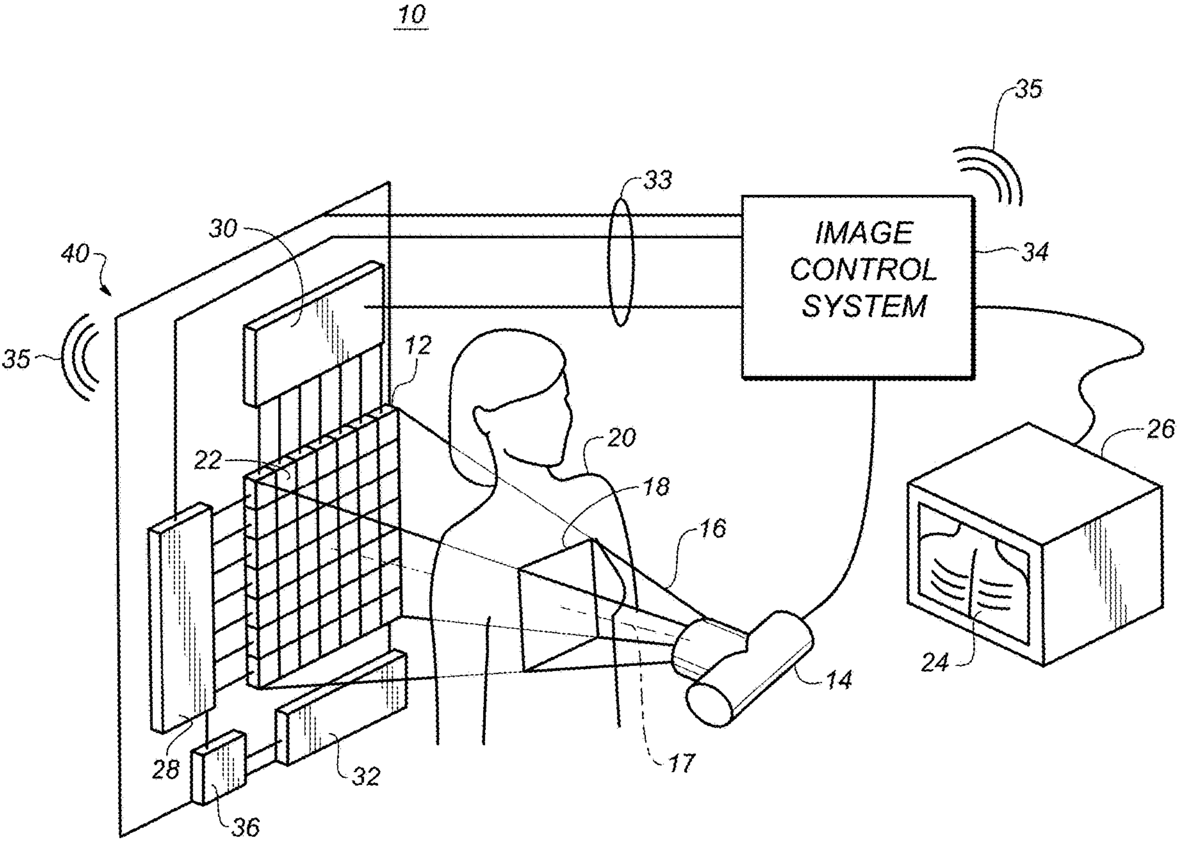
FIG. 1 is a schematic perspective view of an exemplary x-ray imaging device.

FIG. 1 is a perspective view of a digital radiographic (DR) imaging device 10 that may include a curved or planar DR detector 40 (shown in an embodiment that is planar and without an enclosure), an x-ray source 14 configured to generate radiographic energy (x-ray radiation) and having a collimator 15 to shape the emitted x-ray beam 16, and an imaging control system 34 that may include a digital monitor, or electronic display, 26 configured to display images 24 captured by the DR detector 40. The imaging control system 34 controls operation of the (DR) imaging device 10, such as by transmitting signals over a cable 19 to the x-ray source 14 to controllably time and fire the x-ray source 14 according to one embodiment, as described herein. The DR detector 40 may include an image receptor 12 including a two dimensional array of detector cells 22 (imaging pixels or photosensors), arranged in electronically addressable rows and columns. The DR detector's image receptor 12 may be positioned to receive the collimated x-ray beam 16 passing through a patient 20, such as during a fluoroscopy imaging procedure, as emitted by the x-ray source 14. As shown in FIG. 1, the radiographic imaging system 10 may use an x-ray source 14 that emits the collimated x-rays, e.g. the x-ray beam 16, selectively shaped, aimed at, and passing through a preselected portion 18 of patient 20 such that the emitted x-ray beam 16 falls entirely within the imaging region, i.e., the image receptor 12, of the DR detector 40. Some imaging devices may not be configured to secure in a fixed position the relative spatial relationship as between the x-ray source 14 and the DR detector 40. Such imaging devices may include a movable x-ray source 14 attached to a mobile x-ray device cart or to a ceiling-attached movable tube crane, for example. Similarly, the DR detector 40 used with such imaging devices may be unattached to the x-ray source 14 and be freely manually positionable by an operator in relation thereto.

The x-ray beam 16 may be attenuated by varying degrees along its plurality of rays according to the structure, e.g., varying thickness, of the patient 20, which attenuated x-rays are detected by the image receptor 12 to form a digital image. The curved or planar DR detector 40 may be positioned, as much as possible, in a perpendicular relation to a central ray 17 of the x-ray beam 16. The individual imaging pixels 22 may be electronically addressed (scanned) once, or several times per second, by their position according to column and row. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Each individual imaging pixel 22 may be scanned by readout circuitry 28, 30, described herein, to determine a stored voltage level generated therein by the incoming x-ray beam 16. The voltage level stored in each imaging pixel 22 may be read out by the readout circuitry 28, 30, and stored electronically as a digitized numerical value. As is well known, an A/D converter may be used to convert the stored voltage level in each pixel 22 into a digital value. A higher numerical value may be understood to represent a greater amount of x-ray energy absorbed by an individual imaging pixel 22 such as during a fluoroscopic imaging procedure of the patient 20.

In one exemplary embodiment, the rows of photosensitive cells 22 may be scanned one or more at a time by electronic scanning circuit 28 so that the exposure data from the imaging receptor 12 may be transmitted to electronic readout circuit 30. Each photosensitive cell 22 may independently store a charge proportional to an intensity, or energy level, of the attenuated radiographic radiation, or x-rays, received and absorbed in the cell. Thus, each photosensitive cell 22, when read-out, provides information defining a pixel of a radiographic image 24, e.g. a brightness level or an amount of energy absorbed by the pixel, that may be digitally decoded by imaging control system 34 and transmitted to be displayed by the digital monitor 26 for viewing by a user. An electronic bias circuit 32 may be electrically connected to the image receptor 12 to provide a bias voltage to each of the photosensitive cells 22.

The DR detector 40 may communicate with the imaging control system 34 over a connected cable 33 (wired), or the DR detector 40 and the imaging control system 34 may be equipped with a wireless transmitter and receiver to transmit radiographic image data wirelessly 35 to the imaging control system 34. The imaging control system 34 may include a processor and electronic memory (not shown) to control operations of the imaging device 10, as described herein, including control of circuits 28, 30, and 32, for example, by use of programmed instructions, and to store and process image data. The imaging control system 34 may also be used to control activation of the x-ray source 14 using communication cable 19 during a fluoroscopic procedure, controlling an x-ray tube electric current magnitude, and thus the fluence of x-rays in x-ray beam 16, and/or the x-ray tube voltage, and thus the energy level of the x-rays in x-ray beam 16. A portion or all of the imaging control system 34 functions may reside in the DR detector 40 in an on-board processing system 36 which may include a processor and electronic memory to control operations of the DR detector 40 as described herein, including control of circuits 28, 30, and 32, by use of programmed instructions, and to store and process image data similar to the functions of standalone imaging control system 34. The image processing system 36 may control image transmission and image processing and image correction on board the detector 40 based on instructions or other commands transmitted from the imaging control system 34, and transmit corrected digital image data therefrom.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, may be disposed over the light sensitive sensing elements to convert incident x-ray radiographic energy to visible light energy. Thus, in the embodiments disclosed herein, it should be noted that the image receptor 12 (or DR detector 300 in FIG. 3 or DR detector 400 in FIG. 4) may include an indirect or direct type of image receptor.

Examples of sensing elements used in image receptor 12 include various types of photoelectric conversion devices (e.g., photosensors) such as photodiodes (P-N or PIN diodes), photo-capacitors (MIS), photo-transistors or photoconductors. Examples of switching elements used for signal read-out include a-Si TFTs, oxide TFTs, MOS transistors, bipolar transistors and other p-n junction components.

Figure 2:
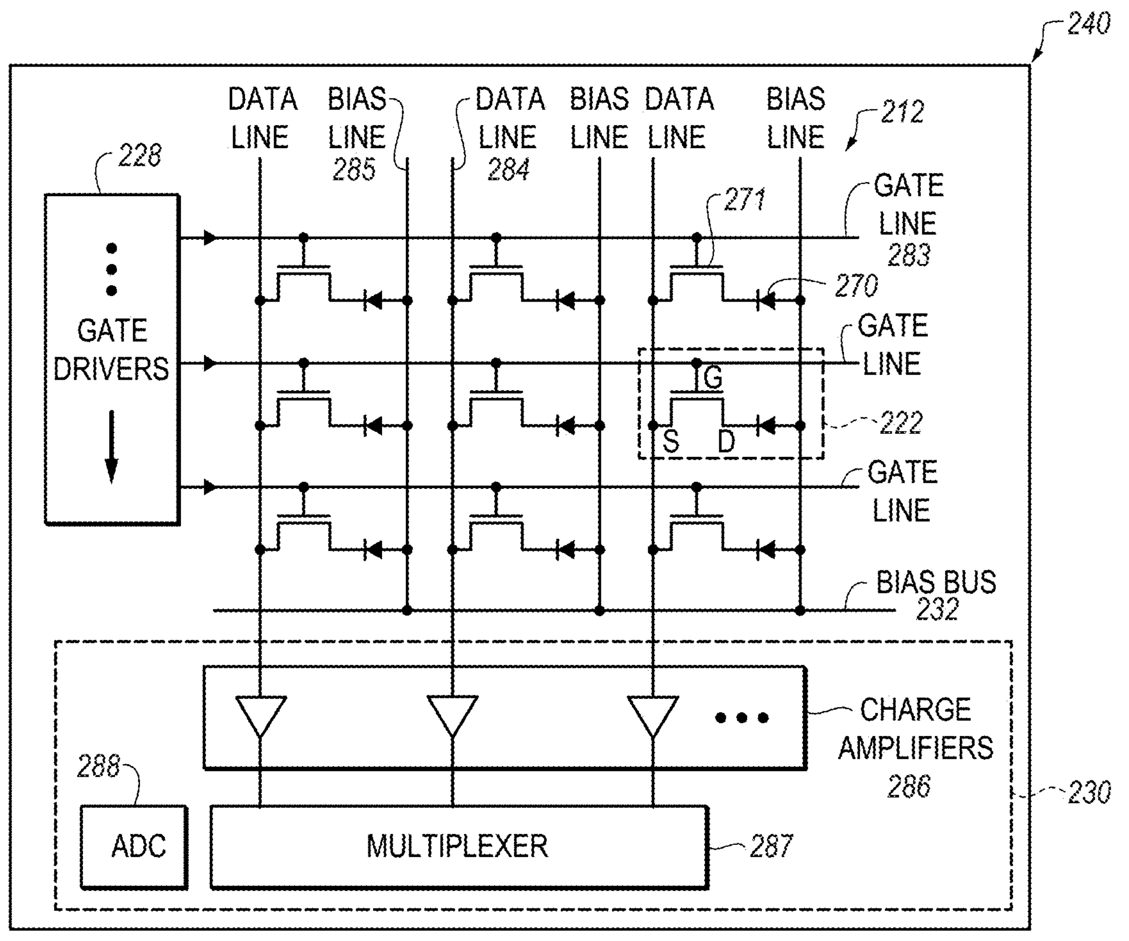
FIG. 2 is a schematic diagram of an exemplary two dimensional imaging pixel array in a digital radiographic (DR) detector.

FIG. 2 is a schematic diagram 240 of a portion of image receptor 12. The array of photosensor cells 212, whose operation may be consistent with the image receptor 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of an image receptor 12 disclosed herein, the two-dimensional array of photosensor cells 22 may be formed in a device layer that abuts adjacent layers of the DR detector structure, which adjacent layers may include a rigid glass layer or a flexible polyimide layer or a layer including carbon fiber without any adjacent rigid layers. A plurality of gate driver circuits 228 may be electrically connected to a plurality of gate lines 283 which control a voltage applied to the gates of TFTs 271. A plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of an image receptor 12 such as an a-Si:H based indirect flat receptor, curved receptor, or flexible image receptor.

In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 can control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the pn junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by imaging control system 34 to yield a digital image which may then be digitally stored and/or immediately displayed on monitor 26 at rates of multiple image frames per second, e.g., 30 fps, such as in a fluoroscopy exam. The DR detector 40 having an image receptor 12 as described herein may be capable of both single-shot, e.g., static, radiographic, and continuous, e.g., fluoroscopic, image acquisition and display.

Figure 3:
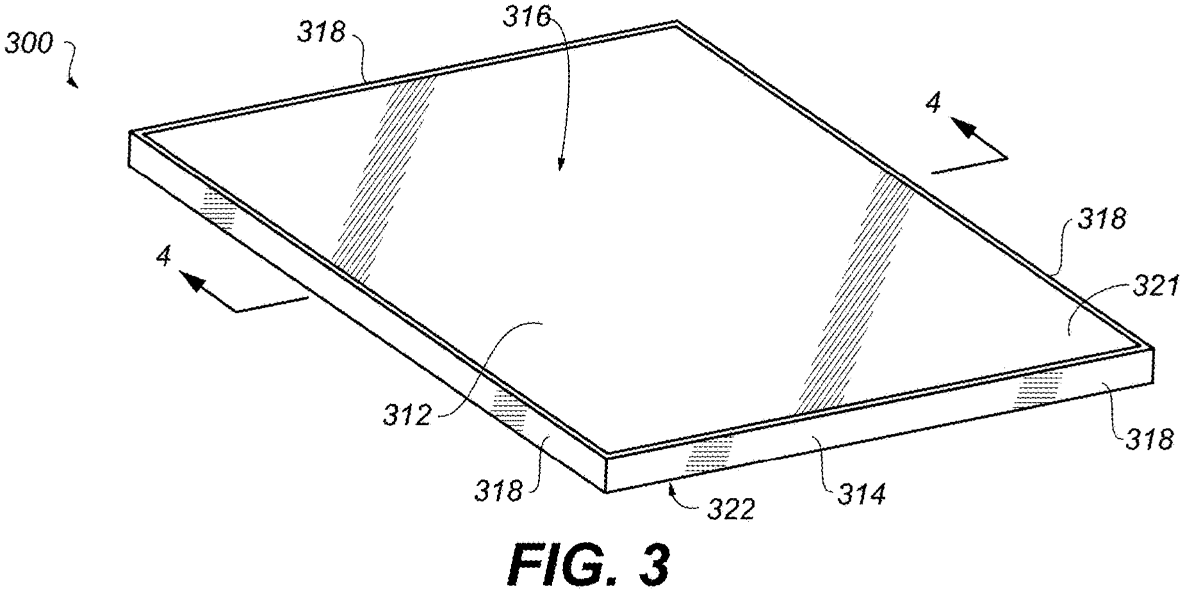
FIG. 3 is a perspective diagram of an exemplary DR detector.

FIG. 3 shows a perspective view of an exemplary portable wireless DR detector 300 according to one embodiment of DR detector 40 disclosed herein. The DR detector 300 may include a flexible substrate to allow the DR detector to capture radiographic images in a curved orientation. The flexible substrate may be fabricated in a permanent curved orientation, or it may remain flexible throughout its life to provide an adjustable curvature, as desired. The DR detector 300 may include a similarly flexible housing portion 314 that surrounds a multilayer structure comprising an image receptor 12 of the DR detector 300. The housing portion 314 of the DR detector 300 may include a continuous, rigid or flexible, radiopaque material, surrounding the image receptor 12 in an interior volume of the DR detector 300. The housing portion 314 may include four flexible edges 318, extending between the top side 321 and the bottom side 322, and arranged substantially orthogonally in relation to the top and bottom sides 321, 322. The bottom side 322 may be continuous with the four edges and disposed opposite the top side 321 of the DR detector 300. The top side 321 comprises a radiolucent top cover 312 attached to the housing portion 314 which, together with the housing portion 314, substantially encloses the multilayer structure in the interior volume of the DR detector 300. The top cover 312 may be attached to the housing 314 to form a seal therebetween, and be made of a radiolucent material that passes x-rays 316 without significant attenuation thereof, such as a carbon fiber plastic, polymeric, or other plastic based material.

Figure 4:
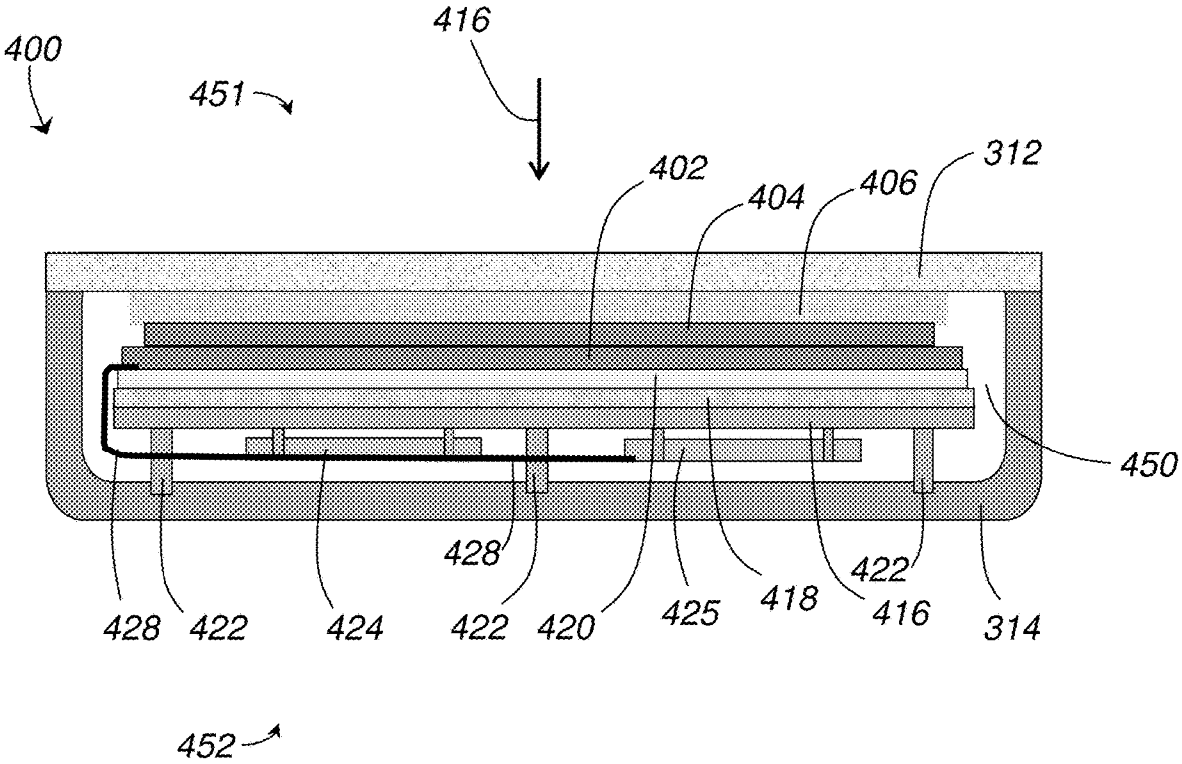
FIG. 4 is a cross section diagram of an exemplary DR detector.

With reference to FIG. 4, there is illustrated in schematic form an exemplary DR detector 400, which may represent a cross-section view along section 4-4 of the exemplary embodiment of the DR detector 300 (FIG. 3). For spatial reference purposes, one major surface of the DR detector

400 may be referred to as the top side 451 and a second major surface may be referred to as the bottom side 452, as used herein. The multilayer structure may be disposed within the interior volume 450 enclosed by the housing 314 and top cover 312 and may include a flexible curved or planar scintillator layer 404 over a curved or planar image receptor 12 shown schematically as the device layer, or imaging array, 402. The scintillator layer 404 may be directly under (e.g., directly connected to) the substantially planar top cover 312, and the device layer 402 may be directly under the scintillator 404. Alternatively, a flexible layer 406 may be positioned between the scintillator layer 404 and the top cover 312 as part of the multilayer structure to allow adjustable curvature of the multilayer structure and/or to provide shock absorption. The flexible layer 406 may be selected to provide an amount of flexible support for both the top cover 312 and the scintillator 404, and may comprise a foam rubber type of material.

A substrate layer 420 may be disposed under the imaging array 402, such as a rigid glass layer, in one embodiment, or flexible substrate comprising polyimide or carbon fiber upon which the imaging array 402 of photosensors may be formed to allow adjustable curvature of the array. Under the substrate layer 420 a radio-opaque shield layer 418 may be used as an x-ray blocking layer to help prevent scattering of x-rays passing through the substrate layer 420 as well as to block x-rays reflected from other surfaces in the interior volume 450. Readout electronics, including the scanning circuit 28, the read-out circuit 30, the bias circuit 32, and processing system 36 (all of FIG. 1) may be formed adjacent the imaging array 402 or, as shown, may be disposed below frame support member 416 in the form of integrated circuits (ICs) electrically connected to printed circuit boards 424, 425. The imaging array 402 may be electrically connected to the readout electronics 424 (ICs) over a flexible connector 428 which may comprise a plurality of flexible, sealed conductors known as chip-on-film (COF) connectors. X-ray flux 416 may pass through the radiolucent top panel cover 312 and impinge upon scintillator 404 where stimulation by the high-energy x-rays 16, or photons, causes the scintillator 404 to emit lower energy photons as visible light rays which are then received in the photosensors of imaging array 402. The frame support member 416 may connect the multilayer structure to the housing 314 using frame support beams 422.

With reference to FIG. 5 and FIG. 6, there is illustrated a barrier assembly 500 for receiving and securing an image receptor 12 or DR detector 40, 300, 400, as described herein. The barrier assembly 500 includes a frame portion, or housing, 501 configured to receive and secure a DR detector 40, 300, 400, or image receptor 12, therewithin in the receiving area 503. Barrier assembly 500 includes electrical connector 505 and a cable 533 electrically connected thereto for establishing digital communication between the secured image receptor 12 or DR detector 40, 300, 400, with a control system of an imaging device 10 via the connector 505 and cable 533. Image receptor 12 or DR detector 40, 300, 400, includes an electrical connector 506 configured to electrically engage the electrical connector 505 when the image receptor 12 or DR detector 40, 300, 400, is positioned in the receiving area 503. Electrical connector 506 is electrically connected to the on-board processor 36 of the image receptor 12 or DR detector 40, 300, 400, to enable digital communication therewith. Electrical connector 505 may be configured to store a digital code capable of being transmitted over cable 533 for identifying barrier assembly 500 via cable 533. Electrical connector 505 may be further configured to transmit such a digital code over cable 533 only when the image receptor 12 or DR detector 40, 300, 400, is fully positioned in the barrier assembly 500. The barrier assembly 500 may be made of a material sufficiently flexible in the receiving area 503 to grip the edges of DR detector 40, 300, 400, or image receptor 12. The barrier assembly 500 may include a handle portion 507 for manually transporting the secured DR detector 40, 300, 400, or image receptor 12. The barrier assembly includes a radiopaque layer, or sheet, 509, made from a material such as lead, embedded as a layer within the barrier assembly housing 501. The radiopaque layer 509 extends beyond all the edges of the image receptor receiving area 503, as shown in the view of FIG. 5, and beyond the edges of the secured image receptor 12 or DR detector 40, 300, 400, as shown in the view of FIG. 8.

FIG. 7A is a cross section view showing how DR detector 40, 300, 400, or image receptor 12, may be inserted or positioned into the barrier assembly 500 of FIG. 7B. As shown in FIG. 7B, a cross-section view along section 7B-7B of the barrier assembly 500 of FIG. 5 illustrates that receiving area 503 may receive and secure the DR detector 40, 300, 400, or image receptor 12, positioned therein. FIG. 7C is a cross section view of the DR detector 40, 300, 400, or image receptor 12, finally positioned in the barrier assembly.

Figure 8:
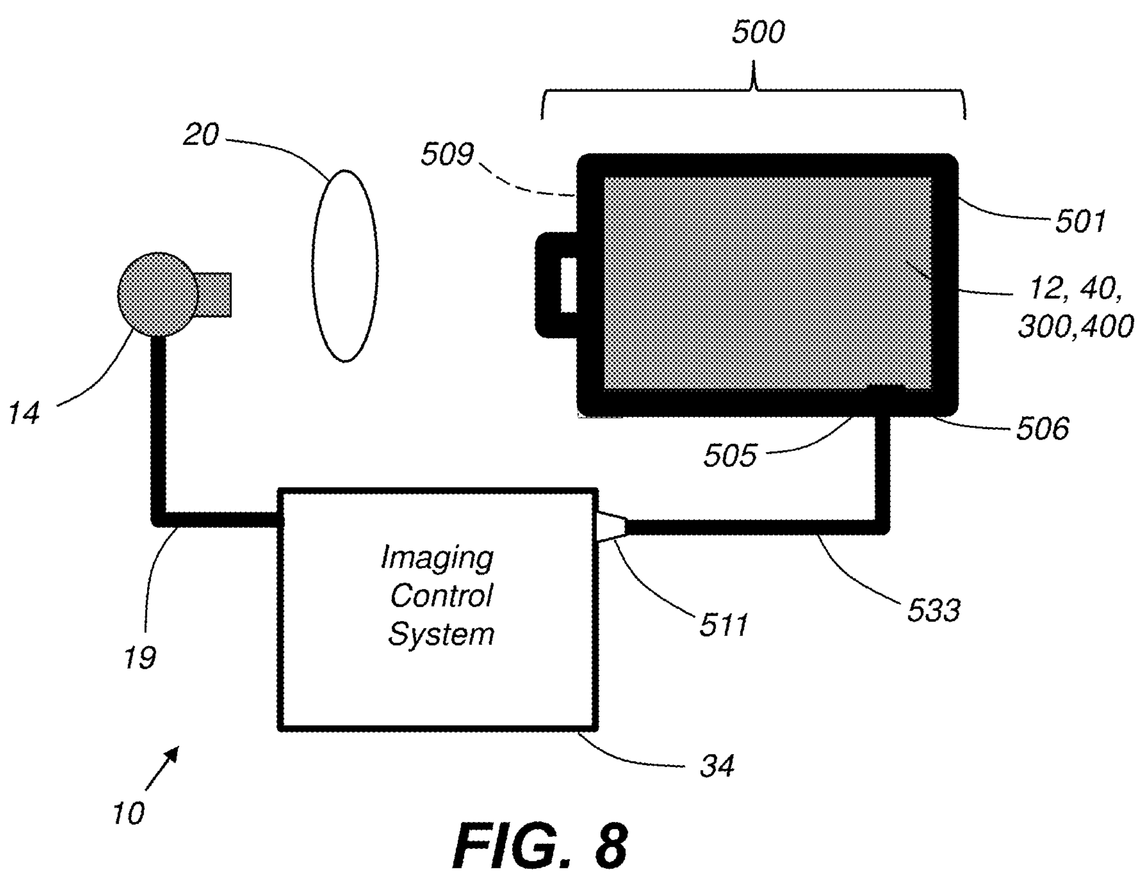
FIG. 8 is a schematic diagram showing the barrier assembly connected to the x-ray imaging device.

FIG. 8 illustrates another schematic diagram of the digital radiographic (DR) imaging device 10 of FIG. 1, wherein image receptor 12 or DR detector 40, 300, 400, is shown secured in barrier assembly 500. Electrical connectors 505, 506, are electrically engaged to establish digital communication between image receptor 12 or DR detector 40, 300, 400, and the imaging control system 34 via cable 533. In one embodiment, cable 533 is permanently attached to electrical connector 505. In one embodiment, imaging control system 34 may be configured to detect, over cable 533, that image receptor 12 or DR detector 40, 300, 400, is fully positioned in the barrier assembly 500 when electrical connectors 505, 506, are electrically engaged. In one embodiment, imaging control system 34 may receive the digital code transmitted over cable 533 for identifying barrier assembly 500, together with a digital signal from the image receptor 12 or DR detector 40, 300, 400, indicating to the imaging control system that image receptor 12 or DR detector 40, 300, 400, is fully positioned in the barrier assembly 500. In one embodiment, imaging control system 34 may receive the digital code transmitted over cable 533 from barrier assembly 500 indicating that the image receptor 12 or DR detector 40, 300, 400, is fully positioned in the barrier assembly 500. In one embodiment, a unique cable connector 511 attached to cable 533 may be configured to uniquely mate with a corresponding connector on imaging control system 34, thereby indicating to the imaging control system 34 that the barrier assembly 500 is connected thereto. Afterwards, any signal from the image receptor 12 or DR detector 40, 300, 400, received over cable 533 signifies that the image receptor 12 or DR detector 40, 300, 400, is fully positioned in the barrier assembly 500.

Figure 9:
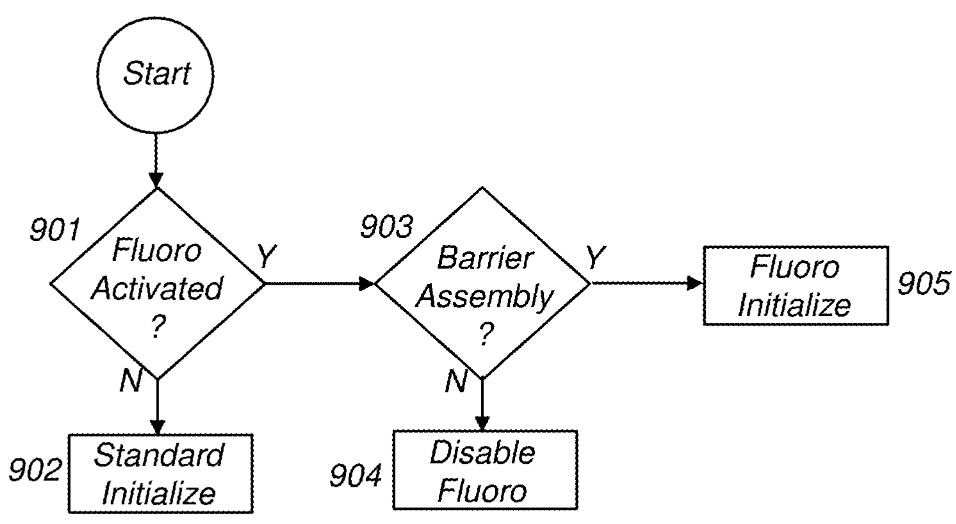
FIG. 9 is a flow diagram for operating an exemplary imaging device.

When the imaging device 10 is initially activated for use in a fluoroscopy mode, image control system 34 is programmed to detect that image receptor 12 or DR detector 40, 300, 400, is fully positioned in barrier assembly 500. In response, imaging control system 34 permits further initiation of the fluoroscopy mode for use by imaging device 10. If the image receptor 12 or DR detector 40, 300, 400, is otherwise connected to image control system 34 without being connected to barrier assembly 500, imaging control system 34 may be configured to allow static imaging, but imaging control system 34 will disable the fluoroscopy mode of imaging device 10. FIG. 9 is an exemplary flow diagram of an algorithm for operating imaging system 10. At step 901, if an operator of imaging device 10 does not select a fluoroscopy mode, the imaging device proceeds with a standard initialization sequence, at step 902. When an operator of the imaging device 10 activates a fluoroscopy imaging mode in step 901, such as by selecting a fluoro mode via a user interface of the imaging device 10, the imaging device 10 determines whether the image receptor 12 or DR detector 40, 300, 400, to be used in the fluoroscopy mode is fully positioned in a barrier assembly 500, at step 903. If the imaging device 10 determines that the image receptor 12 or DR detector 40, 300, 400, is fully positioned in a barrier assembly 500, the imaging system 10 proceeds to initialize the fluoroscopy mode in imaging device 10, at step 905. If the imaging device 10 determines that the image receptor 12 or DR detector 40, 300, 400, is not fully positioned in a barrier assembly 500, the imaging system 10 proceeds to disable the fluoroscopy mode in imaging device 10, at step 904, such as by powering down the x-ray source 14 and displaying a status message on electronic display 26, until the barrier assembly is properly detected by the imaging device 10.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Python, C++ or the like and/or other conventional procedural programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of operating a digital radiographic imaging system comprising the steps of:

communicatively coupling a digital radiographic detector to the digital radiographic imaging system;

the digital radiographic imaging system determining that a fluoroscopy imaging mode is not selected and initializing the digital radiographic imaging system in a standard static imaging mode;

selecting the fluoroscopy imaging mode in the digital radiographic imaging system and the digital radiographic imaging system disabling the selected fluoroscopy mode in response to determining that the digital radiographic detector is not inserted into a barrier assembly;

inserting the digital radiographic detector into the barrier assembly and selecting the fluoroscopy mode in the digital radiographic imaging system; and the digital radiographic imaging system and the digital radiographic detector capturing fluoroscopic images of a patient in response to the digital radiographic imaging system determining that the digital radiographic detector is inserted into the barrier assembly, wherein the barrier assembly comprises a radiopaque material extending beyond all borders of the digital radiographic detector.

2. The method of claim 1, further comprising capturing static radiographic images of the patient using the digital radiographic detector and the digital radiographic imaging system after the step of initializing the digital radiographic imaging system in the standard static imaging mode.

3. The method of claim 2, wherein the digital radiographic imaging system determining that the digital radiographic detector is inserted in the barrier assembly comprises the digital radiographic imaging system receiving a digital signal transmitted from the digital radiographic detector indicating that the digital radiographic detector is inserted in the barrier assembly.

4. A method of operating a digital radiographic imaging system comprising the steps of:

electrically connecting a digital radiographic detector to the digital radiographic imaging system;

the digital radiographic imaging system determining whether a fluoroscopy mode is selected in the digital radiographic imaging system and, if the fluoroscopy mode is determined not to be selected, the digital radiographic imaging system initializing a standard static radiographic imaging mode in the digital radiographic imaging system and, if the fluoroscopy mode is determined to be selected, determining whether the digital radiographic detector is inserted into a barrier assembly and not initializing the standard static radiographic imaging mode in the digital radiographic imaging system;

in response to determining that the fluoroscopy mode is selected in the digital radiographic imaging system and that the digital radiographic detector is not inserted into the barrier assembly, the digital radiographic imaging system disabling the selected fluoroscopy mode; and in response to determining that the fluoroscopy mode is selected in the digital radiographic imaging system and that the digital radiographic detector is inserted into the barrier assembly, the digital radiographic imaging system initializing the fluoroscopy mode in the digital radiographic imaging system, wherein the barrier assembly comprises a radiopaque material extending beyond all borders of the digital radiographic detector.

5. The method of claim 4, wherein the step of the digital radiographic imaging system initializing the fluoroscopy mode in the digital radiographic imaging system further comprises the digital radiographic imaging system and the digital radiographic detector capturing fluoroscopic images of a patient.

6. The method of claim 4, wherein the step of the digital radiographic imaging system initializing a standard static radiographic imaging mode in the digital radiographic imaging system further comprises the digital radiographic imaging system and the digital radiographic detector capturing standard static radiographic images of a patient.

7. The method of claim 4, wherein the step of determining that the digital radiographic detector is inserted into the barrier assembly comprises the digital radiographic imaging system receiving a digital signal transmitted from the digital radiographic detector indicating that the digital radiographic detector is inserted into the barrier assembly.

8. A method of operating a digital radiographic imaging system comprising the steps of:

electrically connecting a digital radiographic detector to the digital radiographic imaging system;

capturing standard static radiographic images of a patient using the digital radiographic detector and the digital radiographic imaging system;

selecting a fluoroscopy mode in the digital radiographic imaging system and the digital radiographic imaging system disabling the selected fluoroscopy mode in response to determining that the digital radiographic detector is not positioned in a barrier assembly;

inserting the digital radiographic detector into the barrier assembly and selecting the fluoroscopy mode in the digital radiographic imaging system; and the digital radiographic imaging system and the digital radiographic detector capturing fluoroscopic images of the patient in response to the digital radiographic imaging system determining that the digital radiographic detector is positioned in the barrier assembly, whereby the barrier assembly comprises a radiopaque material extending beyond all borders of the digital radiographic detector.

9. The method of claim 8, wherein the step of determining that the digital radiographic detector is positioned in the barrier assembly comprises the digital radiographic imaging system receiving a digital signal transmitted from the digital radiographic detector indicating that the digital radiographic detector is positioned in the barrier assembly.

* * * * *